(12) United States Patent
Adkins et al.

(10) Patent No.: US 7,196,209 B2
(45) Date of Patent: Mar. 27, 2007

(54) CONTINUOUS PROCESS FOR THE PREPARATION OF FRUCTOPYRANOSE SULFAMATE DERIVATIVES

(75) Inventors: Thomas W. Adkins, Austinburg, OH (US); Charles F. Cicco, Cleveland Heights, OH (US); Penina Feibush, Ambler, PA (US); Donald A. Koch, Painesville, OH (US); Cynthia Maryanoff, New Hope, PA (US); Walter E. Stalzer, Mentor, OH (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 138 days.

(21) Appl. No.: 10/691,782

(22) Filed: Oct. 23, 2003

(65) Prior Publication Data

US 2004/0158081 A1 Aug. 12, 2004

Related U.S. Application Data

(60) Provisional application No. 60/422,558, filed on Oct. 31, 2002.

(51) Int. Cl.
*C07D 493/14* (2006.01)
*C07D 309/06* (2006.01)
*C07C 303/00* (2006.01)
*C07H 9/04* (2006.01)

(52) U.S. Cl. .............. 549/387; 536/17.6; 549/426; 558/48

(58) Field of Classification Search .......... 536/17.6; 558/48; 549/387, 396, 407, 426, 433, 443
See application file for complete search history.

(56) References Cited

U.S. PATENT DOCUMENTS 4,513,006 A 4/1985 Maryanoff et al.
5,387,700 A 2/1995 Maryanoff et al.

OTHER PUBLICATIONS

Maryanoff, B.E. et al.: "Structure-Activity Studies on anticonvulsant Sugar Sulfamates Related to Topiramate. Enhanced Potency with Cyclic Sulfate Derivatives". Journal of Medicinal Chemistry, American Chemical Society. Washington, U.S., vol. 41, No. 8, 1998, pp. 1315-1343.
Kyowa, H.: "Topiramate". Drugs of the Future, Barcelona, ES, vol. 21, No. 4, 1996, pp. 463-465.

*Primary Examiner*—Bernard Dentz
(74) *Attorney, Agent, or Firm*—Mary Appollina

(57) ABSTRACT

The present invention is directed to a continuous process for the preparation of fructopyranose sulfamate derivatives of the general formula (I)

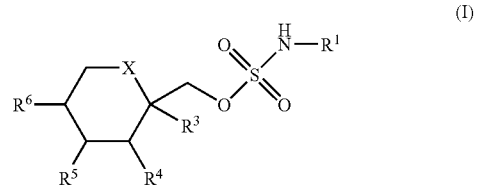

wherein $R^1$, $R^3$, $R^4$, $R^5$, $R^6$ and X are as herein defined. The present invention is further directed to a continuous process for the preparation of Topiramate.

35 Claims, No Drawings

CONTINUOUS PROCESS FOR THE PREPARATION OF FRUCTOPYRANOSE SULFAMATE DERIVATIVES

CROSS REFERENCE TO RELATED APPLICATION

This application claims the benefit of U.S. Provisional Application 60/422,558, filed on Oct. 31, 2002, which is incorporated by reference herein in its entirety.

FIELD OF THE INVENTION

The present invention relates to a continuous process for the preparation of fructopyranose sulfamate derivatives of the general formula (I)

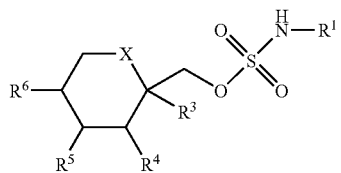

(I)

wherein $R^1$, $R^3$, $R^4$, $R^5$, $R^6$ and X are as hereinafter defined.

BACKGROUND OF THE INVENTION

Sulfamates of the Formula (I)

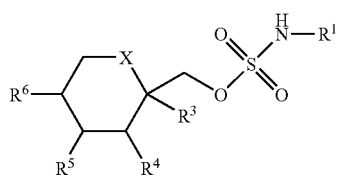

(I)

wherein X is O or $CH_2$ and $R^1$, $R^3$, $R^4$, $R^1$ and $R^6$ are as hereinafter defined, are known compounds that have been found to exhibit anticonvulsant activity and are therefore useful in the treatment of conditions such as epilepsy. These compounds are disclosed in U.S. Pat. Nos. 4,582,916 and 4,513,006, which also disclose processes for the preparation of said compounds; and which are hereby incorporated by reference.

One process disclosed in the above referenced patents is a process for the preparation of the compounds of formula (I) comprising reacting an alcohol of the formula $RCH_2OH$ with a chlorosulfamate of the formula $ClSO_2NH_2$ or $ClSO_2NHR^1$ in the presence of a base such as potassium t-butoxide or sodium hydride at a temperature of about −20° C. to 25° C. and in a solvent such as toluene, tetrahydrofuran or dimethylformamide, where R is a moiety of the formula (II)

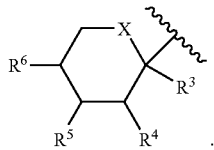

(II)

This process has two major disadvantages, particularly for large scale synthesis. One disadvantage is that the process calls for a combination of NaH and DMF which has an uncontrollable exotherm and is therefore potentially explosive. See J. Buckley et al., Chemical & Engineering News, Jul. 12, 1982, page 5; and G. DeWail, Chemical & Engineering News, Sep. 13, 1982. Another disadvantage is that the process also uses highly toxic and corrosive chlorosulfonyl isocyanate (CSI) to prepare the commercially unavailable sulfamyl chloride ($ClSO_2NH_2$).

Another process for the preparation of compounds of formula (I) disclosed in the above mentioned U.S. Pat. No. 4,513,006 comprises reacting an alcohol of the formula $RCH_2OH$ with sulfuryl chloride of the formula $SO_2Cl_2$ in the presence of a base such as triethylamine or pyridine at a temperature of about −40° C. to 25° C. in a diethyl ether or methylene chloride solvent to produce a chlorosulfate of the formula $RCH_2OSO_2Cl$. The chlorosulfate of the formula $RCH_2OSO_2Cl$ may then be reacted with an amine of the formula $R^1NH_2$ at a temperature of about −40° C. to 25° C. in a methylene chloride or acetonitrile solvent to produce the compound of formula (I). This process utilizing diethyl ether, methylene chloride and acetonitrile solvents produces relatively low yields of the desired end product of formula (I).

A third process disclosed in the two patents mentioned above comprises reacting the chlorosulfate of formula $RCH_2OSO_2Cl$ (formed as previously described) with a metal azide such as sodium azide in a solvent such as methylene chloride or acetonitrile to yield an azidosulfate of the formula $RCH_2OSO_2N_3$. The azidosulfate is then reduced to the compound of formula (I) wherein $R^1$ is hydrogen, by catalytic hydrogenation.

A disadvantage with this process is that explosions may occur when handling the azide compounds. Also, the process contains an additional chemical transformation involving the reduction of the azide to the $NH_2$ moiety.

Maryanoff et al. in U.S. Pat. No. 5,387,700 disclose a process for the preparation of compounds of formula (I) which comprises reacting an alcohol of the formula $RCH_2OH$ with sulfuryl chloride in the presence of a base, in a solvent selected from the group consisting of toluene, t-butyl methyl ether and tetrahydrofuran, to form a chlorosulfate intermediate of the formula $RCH_2OSO_2Cl$. In a second step, the chlorosulfate of formula $RCH_2OSO_2Cl$ is reacted with an amine of the formula $R^1NH_2$, in a solvent selected from the group consisting of tetrahydrofuran, t-butyl methyl ether and lower alkanol (e.g. methanol or ethanol) to form the compound of formula (I).

One disadvantage of this process is that the compound of formula (I) is prepared in a batch process wherein the first reaction is carried out, the solvent is removed, the product is isolated, the isolated solid is re-dissolved in a second solvent and then reacted to the final product. This results in a process which requires isolation of a semi-stable, thermally labile ROSO$_2$Cl intermediate.

It is an object of the present invention to provide a continuous process for the preparation of the compounds of formula (I), which does not require changes in solvent systems, which uses readily available materials, which can be carried out under safe conditions, which will produce relatively high yields and/or which will allow for the production of a greater amount of material per unit time per reactor space (i.e which will allow for production of a greater amount of material in smaller equipment).

SUMMARY OF THE INVENTION

The present invention is directed to a continuous process for the preparation of compounds of formula (I)

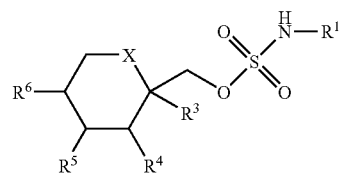
(I)

wherein

X is selected from CH$_2$ or O;

R$^1$ is selected from the group consisting of hydrogen and C$_{1-4}$alkyl;

R$^3$, R$^4$, R$^5$ and R$^6$ are each independently selected from hydrogen or lower alkyl and, when X is CH$_2$, R$^5$ and R$^6$ may be alkene groups joined to form a benzene ring and, when X is O, R$^3$ and R$^4$ and/or R$^5$ and R$^6$ together may be a methylenedioxy group of the formula:

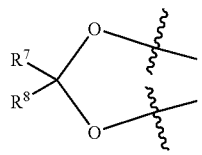

wherein

R$^7$ and R$^8$ are same or different and are hydrogen, lower alkyl or are alkyl and are joined to form a cyclopentyl or cyclohexyl ring;

comprising

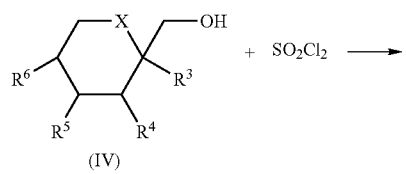

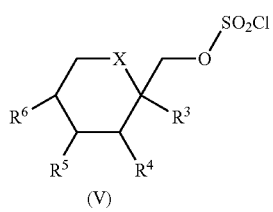
(V)

(A) reacting a suitably substituted compound of formula (IV) with sulfuryl chloride;

in the presence of an organic or inorganic base;

in a first organic solvent comprising at least one solvent selected from a cyclic ether, a straight or branched chain dialkyl ether, an aromatic hydrocarbon, or a mixture of a cyclic, straight or branched chain dialkyl ether and an aromatic hydrocarbon solvent;

to form the corresponding compound of formula (V);

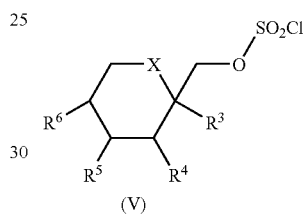 
(V)              (VI)

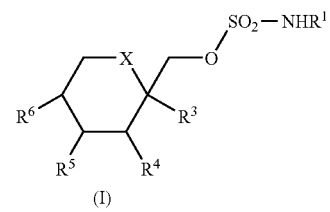
(I)

(B) reacting the compound of formula (V) with a suitably substituted compound of formula (VI);

in a second organic solvent comprising at least the solvent used in step (A);

to form the corresponding compound of formula (I).

The present invention is further directed to a continuous process for the preparation of the compound of formula (III)

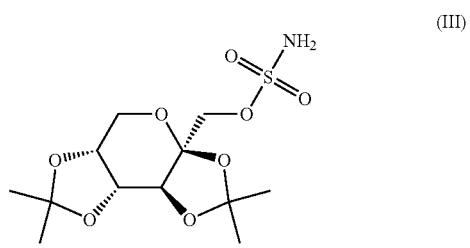
(III)

also known as topiramate, a compound of formula (I) wherein X is O, R$^1$ is hydrogen, R$^3$ and R$^4$ and R$^5$ and R$^6$ are each taken together to form comprising

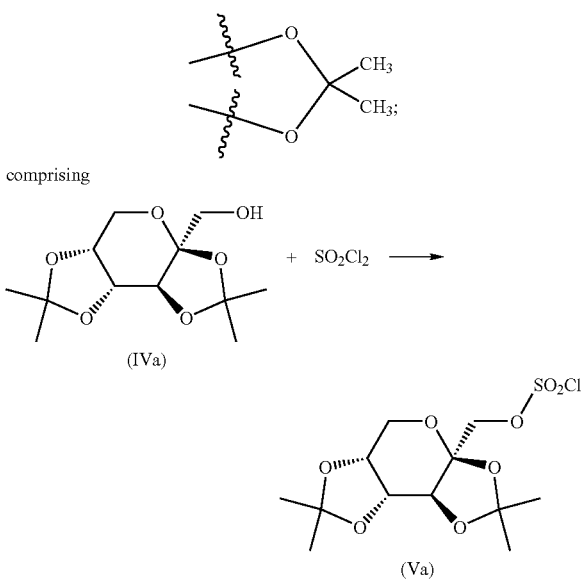

(Aa) reacting a compound of formula (IVa) with sulfuryl chloride;

in the presence of an organic or inorganic base;

in a first organic solvent comprising at least one solvent selected from a cyclic ether, a straight or branched chain dialkyl ether, an aromatic hydrocarbon, or a mixture of a cyclic, straight or branched chain dialkyl ether and an aromatic hydrocarbon solvent;

to form the corresponding compound of formula (Va);

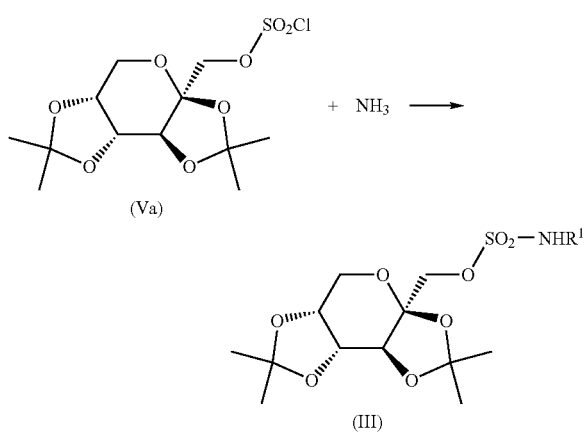

(Ba) reacting the compound of formula (Va) with ammonia;

in a second organic solvent comprising at least the solvent used in step (A);

to form the corresponding compound of formula (III).

The present invention is further directed to a compound prepared according to any of the processes described herein.

Illustrative of the invention is a pharmaceutical composition comprising a pharmaceutically acceptable carrier and a compound prepared according to any of the processes described above.

An illustration of the invention is a pharmaceutical composition made by mixing a pharmaceutically acceptable carrier and a compound prepared according to any of the processes described above.

Illustrating the invention is a process for making a pharmaceutical composition comprising mixing a pharmaceutically acceptable carrier and a compound prepared according to any of the processes described above.

Another example of the invention is the use of a compound prepared according to any of the processes described herein in the preparation of a medicament for treating epilepsy.

DETAILED DESCRIPTION OF THE INVENTION

In an embodiment of the present invention, the second organic solvent (used in step (B)) is the same as the first organic solvent (used in step (A)). In another embodiment of the present invention, the first organic solvent (used in step (A)) and the second organic solvent (used in step (B)) are both glyme.

As used herein, the term "reactor" shall mean a continuous reactor, for example a continuous stirred tank reactor (CSTR), a plug flow reactor, a tower reactor, and the like. Preferably, the continuous reactor is a continuous stirred tank reactor.

As used herein, the term "residence time" shall mean the average amount of time a particle of reactant or reactants spends within the reactor.

As used herein, the term "alkyl" whether used alone or as part of a substituent group, include straight and branched alkyl chains. For example, alkyl radicals include methyl, ethyl, propyl, isopropyl, butyl, isobutyl, sec-butyl, t-butyl, pentyl and the like. Unless otherwise noted, the term "lower" when used with alkyl shall mean a carbon chain composition of 1–4 carbon atoms.

With reference to substituents, the term "independently" means that when more than one of such substituents is possible, such substituents may be the same or different from each other.

When a particular group is "substituted" (e.g., alkyl, phenyl, aryl, aralkyl, heteroaryl), that group may have one or more substituents, preferably from one to three substituents, more preferably from one to two substituents, independently selected from the list of substituents.

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Abbreviations used in the specification, particularly the Schemes and Examples, are as follows:

CS or=Diacetone-β-D-fructose chlorosulfate chlorosulfate
CSTR=Continuous stirred tank reactor
DAF=Diacetone-β-D-fructose DIPEA=Diisopropylethylamine
DMF=N,N-Dimethylformamide
GC=Gas Chromatography
glyme=Ethylene glycol dimethyl ether
HPLC=High pressure liquid chromatography
MTBE=Methyl-t-butyl ether
SC=Sulfuryl chloride
TEA=Triethylamine
THF=Tetrahydrofuran
TPM=Topiramate The present invention is directed to a continuous process for the preparation of a compound of formula (I)

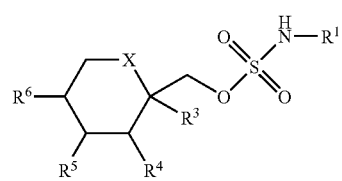

(I)

wherein

X is selected from $CH_2$ or O;

$R^1$ is selected from the group consisting of hydrogen and $C_{1-4}$alkyl;

$R^3$, $R^4$, $R^5$ and $R^6$ are each independently selected from hydrogen or lower alkyl and, when X is $CH_2$, $R^5$ and $R^6$ may be alkene groups joined to form a benzene ring and, when X is O, $R^3$ and $R^4$ and/or $R^5$ and $R^6$ together may be a methylenedioxy group of the formula:

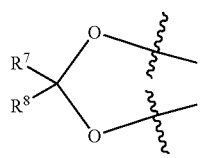

wherein $R^7$ and $R^8$ are the same or different and are hydrogen, lower alkyl or are alkyl and are joined to form a cyclopentyl or cyclohexyl ring.

More particularly, the present invention is directed to a continuous process for the preparation of a compound of formula (I) as outlined in Scheme 1.

Scheme I

Step (A):

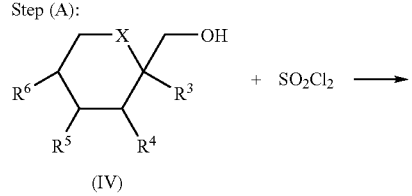 + $SO_2Cl_2$ →

(IV)

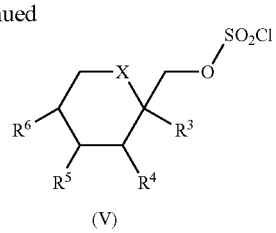

(V)

Step (B):

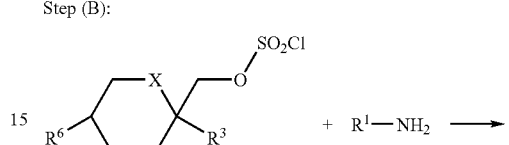

(V)                (VI)

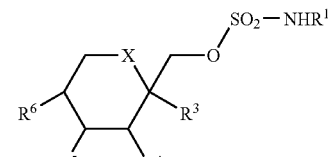

(I)

Accordingly, in step (A), a suitably substituted compound of formula (IV), a known compound or compound prepared by known methods, and a base are dissolved in a first organic solvent, and reacted with sulfuryl chloride;

wherein the base is an inorganic base such as $Na_2CO_3$, $K_2CO_3$, $NaHCO_3$, and the like, or an organic base such as a tertiary amine base such as pyridine, a pyridine derivative, TEA, DIPEA, and the like; preferably an organic tertiary amine base, more preferably pyridine;

wherein, preferably the base does not react with the compound of formula (IV) or the sulfuryl chloride;

wherein the first organic solvent comprises at least one solvent selected from a cyclic ether, such as pyran, tetrahydrofuran, and the like; a straight or branched chain dialkyl ether such as glyme, MTBE, and the like; an aromatic hydrocarbon solvent such as toluene, benzene, xylene, and the like; or a mixture of a cyclic, straight or branched chain dialkyl ether and an aromatic hydrocarbon solvent; preferably the first organic solvent comprises at least one solvent selected from a cyclic or straight or branched chain dialkyl ether such as THF, pyran, glyme, MTBE, and the like; more preferably the first organic solvent comprises at least glyme;

wherein the sulfuryl chloride is preferably present in an amount greater than about 0.9 moles per mole of the compound of formula (IV); more preferably, the molar ratio of the compound of formula (IV) to the sulfuryl chloride is in the range of from about 1:0.9 to about 1:1.5; more preferably still, the molar ratio of the compound of formula (IV) to the sulfuryl chloride is in the range of from about 1:1.0 to about 1:1.05;

wherein the base is preferably present in an amount greater than about 1 molar equivalent of the compound of formula (IV); more preferably, the molar ratio of the compound of formula (IV) to the base is greater than or equal to about 1:1.05; more preferably still, the molar ratio of the compound of formula (IV) to the base is in the range of from about 1:1.05 to about 1:1.20; more preferably still, the molar ratio of the compound of formula (IV) to the base is about 1:1.05;

wherein the temperature of the reaction is preferably maintained at less than about 50° C., more preferably at about 0° C. to about 20° C., most preferably at about 0° C.;

to form a solution containing the corresponding compound of formula (V) and a precipitate of the base hydrochloride salt.

In an embodiment of the present invention, the first organic solvent (used in Step (A)) is selected from the group consisting of a cyclic ether, such as pyran, tetrahydrofuran, and the like; a straight or branched chain dialkyl ether such as glyme, MTBE, and the like; an aromatic hydrocarbon solvent such as toluene, benzene, xylene, and the like; or a mixture of a cyclic, straight or branched chain dialkyl ether and an aromatic hydrocarbon solvent. Preferably, the first organic solvent (used in step (A)) is selected from a cyclic or straight or branched dialkyl ether such as THF, pyran, glyme, MTBE, and the like, more preferably the first organic solvent (used in step (A)) is glyme.

In an embodiment of the present invention, the first organic solvent (used in Step (A)) is selected from the group consisting of a cyclic ether, a straight or branched chain dialkyl ether, and an aromatic hydrocarbon solvent; wherein the first organic solvent is other than tetrahydrofuran or t-butyl methyl ether.

In an embodiment of the present invention, step (A) of the reaction is run such that the compound of formula (IV) and the base, dissolved in the first organic solvent, are reacted with neat sulfuryl chloride, by continuously feeding one reaction stream containing the compound of formula (IV) and the base dissolved in the first organic solvent and a second reaction stream containing the sulfuryl chloride into a continuous reactor, preferably a CSTR. In another embodiment of the present invention, the sulfuryl chloride is dissolved in the same organic solvent as that used to dissolve the compound of formula (IV) and the base (i.e. the first organic solvent).

Preferably, the solution containing the compound of formula (V) and the precipitate of the base hydrochloride salt is filtered, according to known methods, to remove the precipitate.

Preferably, the solution containing the compound of formula (V) is concentrated by known batch or continuous methods, for example by evaporation of the solvent (such as by falling film or wiped film evaporation), or by vacuum distillation, to yield a concentrate of the compound of formula (V). In an embodiment of the present invention, the solution containing the compound of formula (V) is concentrated to less than or equal to about half the original mass of the solution. In another embodiment of the present invention, the solution containing the compound of formula (V) is concentrated to an oil.

Wherein the compound of formula (IV) is reacted with greater than about 1 equivalent of sulfuryl chloride, the solution containing the compound of formula (V) is preferably concentrated, according to known batch or continuous method, to remove at least about 70% of solvent mass.

Wherein the compound of formula (IV) is reacted with about 1 equivalent of sulfuryl chloride, the solution containing the compound of formula (V) is preferably concentrated, according to known batch or continuous method, to remove at least about 20% of solvent mass.

In an embodiment of the present invention, the solution containing the compound of formula (V) is treated to remove volatiles. Suitable treatments include, but are not limited to, vacuum distillation, concentration, stripping, passing through activated carbon or other absorbent, and the like.

The concentrate of the compound of formula (V) is dissolved in a second organic solvent comprising at least the solvent used in step (A) (i.e. the first organic solvent), preferably comprising at least one solvent selected from a cyclic ether, such as pyran, tetrahydrofuran, and the like; a straight or branched chain dialkyl ether such as glyme, MTBE, and the like; an aromatic hydrocarbon solvent such as toluene, benzene, xylene, and the like; or a mixture of a cyclic, straight or branched chain dialkyl ether and an aromatic hydrocarbon solvent. Preferably, the concentrate of the compound of formula (V) is dissolved in the same organic solvent used in step (A) above.

Preferably, the concentrate of the compound of formula (V) is dissolved to a final mass ratio of the solvent to the compound of formula (V) in the range of from about 2:1 to about 10:1, more preferably to a mass ratio of the solvent to the compound of formula (V) of about 6:1, to yield a reaction stream for use in step (B), hereinafter referred to as the third reaction stream, containing the compound of formula (V).

In step (B), the compound of formula (V) is reacted with a suitably substituted compound of formula (VI), a known compound or compound prepared by known methods, in a second organic solvent comprising at least the solvent used in step (A);

wherein the second organic solvent comprises at least one solvent selected from a cyclic ether, such as pyran, tetrahydrofuran, and the like; a straight or branched chain dialkyl ether such as glyme, MTBE, and the like; an aromatic hydrocarbon solvent such as toluene, benzene, xylene, and the like; or a mixture of a cyclic, straight or branched chain dialkyl ether and an aromatic hydrocarbon solvent; preferably the second organic solvent comprises at least one solvent selected from a cyclic or straight or branched dialkyl ether such as THF, pyran, glyme, MTBE, and the like; more preferably the second organic solvent comprises at least glyme; more preferably still, the second organic solvent is the same as the first organic solvent; more preferably still, the second organic solvent is glyme;

wherein the compound of formula (VI) is preferably present in an amount greater than about 1 molar equivalent of the compound of formula (V); more preferably, the molar ratio of the compound of formula (VI) to the compound of formula (V) is greater than or equal to about 2:1; more preferably still, the molar ratio of the compound of formula (VI) to the compound of formula (V) is about 5:1;

wherein the temperature of the reaction is preferably maintained in the range of about −30° C. to about 50° C., more preferably in the range of about 0° C. to about 30° C., more preferably still at about 20° C.;

to form a solution of the compound of formula (I) and a precipitate.

When the compound of formula (VI) is ammonia gas, the ammonia gas is preferably fed into the reactor at a controlled pressure or flow rate, more preferably, at a pressure in the range of less than or equal to about 30 psia, more preferably still, at a pressure in a range of about 15 psia to about 20 psia, more preferably still, at a pressure of about 19 psia.

In an embodiment of the present invention, the second organic solvent (used in step (B)) is selected from the group consisting of a cyclic ether, such as pyran, tetrahydrofuran, and the like; a straight or branched chain dialkyl ether such as glyme, MTBE, and the like; an aromatic hydrocarbon solvent such as toluene, benzene, xylene, and the like; or a mixture of a cyclic, straight or branched chain dialkyl ether and an aromatic hydrocarbon solvent. Preferably, the second organic solvent (used in step (B)) is selected from a cyclic or straight or branched chain dialkyl ether such as THF, pyran, glyme, MTBE, and the like, more preferably the second organic solvent (used in step (B)) is glyme.

In an embodiment of the present invention, the second organic solvent (used in Step (B)) is selected from the group consisting of a cyclic ether, a straight or branched chain dialkyl ether and an aromatic hydrocarbon solvent; wherein the second organic solvent is other than tetrahydrofuran or t-butyl methyl ether.

In another embodiment of the present invention, the second organic solvent (used in step (B)) comprises the solvent used in step (A) (i.e. the first organic solvent).

Preferably, the solution containing the compound of formula (I) and the precipitate is filtered by known methods, to remove the precipitate.

In an embodiment of the invention, the process for the preparation of a compound of formula (I) is run in two continuous stirred tank reactors (CSTRs). Preferably, step (A) is run such that the residence time in the first CSTR is about 1 hour. Preferably, step (B) is run such that the residence time in the second CSTR is about 3 hours. Preferably, step (B) is run such that the third reaction stream and the compound of formula (VI) are introduced above surface into the CSTR.

The present invention is further directed to a continuous process for the preparation of a compound of formula (III), also known as Topiramate, as outlined in Scheme 2.

Scheme 2

Step (Aa):

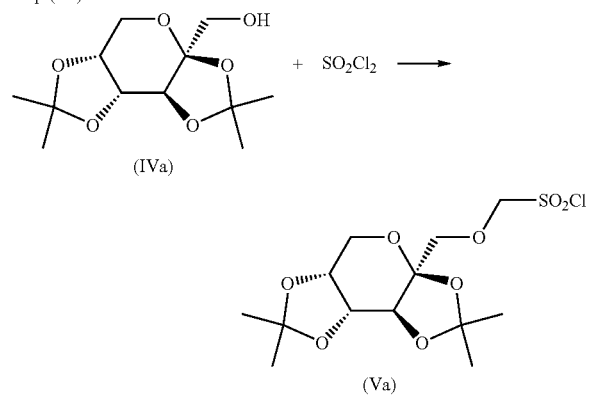

Step (Ba):

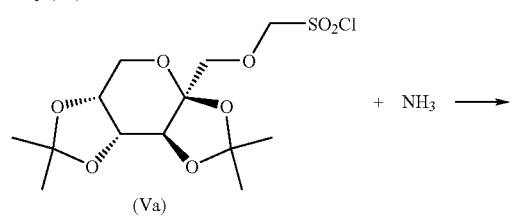

-continued

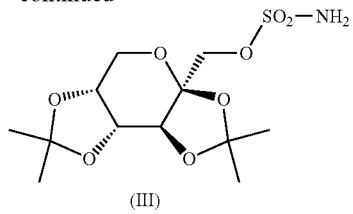

Accordingly, in step (Aa), a compound of formula (IVa), a compound also known as diacetone fructose (DAF), and a base are dissolved in a first organic solvent, and reacted with sulfuryl chloride;

wherein the base is an inorganic base such as $Na_2CO_3$, $K_2CO_3$, $NaHCO_3$, and the like, or an organic base such as a tertiary amine base such as pyridine, a pyridine derivative, TEA, DIPEA, and the like; preferably an organic tertiary amine base, more preferably pyridine;

wherein, preferably the base does not react with the compound of formula (IVa) or the sulfuryl chloride;

wherein the first organic solvent comprises at least one solvent selected from a cyclic ether, such as pyran, tetrahydrofuran, and the like; a straight or branched chain dialkyl ether such as glyme, MTBE, and the like; an aromatic hydrocarbon solvent such as toluene, benzene, xylene, and the like; or a mixture of a cyclic, straight or branched chain dialkyl ether and an aromatic hydrocarbon solvent; preferably the first organic solvent comprises at least one solvent selected from a cyclic or straight or branched chain dialkyl ether such as THF, pyran, glyme, MTBE, and the like; more preferably the first organic solvent comprises at least glyme; more preferably still, the first organic solvent is glyme;

wherein the sulfuryl chloride is preferably present in an amount greater than about 0.9 moles per mole of the compound of formula (Iva); more preferably, the molar ratio of the compound of formula (Iva) to the sulfuryl chloride is in the range of from about 1:0.9 to about 1:1.5; more preferably still, the molar ratio of the compound of formula (IVa) to the sulfuryl chloride is in the range of from about 1:1.0 to about 1:1.05;

wherein the base is preferably present in an amount greater than about 1 molar equivalent relative to the compound of formula (IVa); more preferably, the molar ratio of the compound of formula (Iva) to the base is greater than or equal to about 1:1.05; more preferably, the molar ratio of the compound of formula (IVa) to the base is in the range of from about 1:1.05 to about 1:1.20; more preferably still, the molar ratio of the compound of formula (IVa) to the base is about 1:1.05;

wherein the temperature of the reaction is preferably maintained at less than about 50° C., more preferably at about 0° C. to about 20° C., most preferably at about 0° C.;

to form a solution containing the corresponding compound of formula (Va) and a precipitate of the base hydrochloride salt.

In an embodiment of the present invention, the first organic solvent (used in Step (Aa)) is selected from the group consisting of a cyclic ether, such as pyran, tetrahydrofuran, and the like; a straight or branched chain dialkyl ether such as glyme, MTBE, and the like; an aromatic hydrocarbon solvent such as toluene, benzene, xylene, and the like; or a mixture of a cyclic, straight or branched chain dialkyl ether and an aromatic hydrocarbon solvent. Preferably, the first organic solvent (used in step (Aa)) is selected from a cyclic or straight or branched chain dialkyl ether such as THF, pyran, glyme, MTBE, and the like; more preferably the first organic solvent (used in step (Aa)) is glyme.

In an embodiment of the present invention, the first organic solvent (used in Step (Aa)) is selected from the group consisting of a cyclic ether, a straight or branched chain dialkyl ether and an aromatic hydrocarbon solvent; wherein the first organic solvent is other than tetrahydrofuran or t-butyl methyl ether.

In an embodiment of the present invention, step (Aa) of the reaction is run such that the compound of formula (Iva) and the base dissolved in the first organic solvent system are reacted with neat sulfuryl chloride; by continuously feeding one reaction stream containing the compound of formula (IVa) and the base dissolved in the first organic solvent system and a second reaction stream containing the sulfuryl chloride into a continuous reactor, preferably a CSTR. In another embodiment of the present invention, the sulfuryl chloride is dissolved in the same organic solvent system as that used to dissolve the compound of formula (Iva) and the base (i.e. the first organic solvent).

Preferably, the solution containing the compound of formula (Va) and the precipitate of the base hydrochloride salt is filtered, according to known methods, to remove the precipitate.

Preferably, the solution containing the compound of formula (Va) is concentrated by known batch or continuous methods, for example by evaporation of the solvent (such as by falling film or wiped film evaporation), or by vacuum distillation, to yield a concentrate of the compound of formula (Va). In an embodiment of the present invention, the solution containing the compound of formula (Va) is concentrated to less than or equal to about half the original mass of the solution. In another embodiment of the present invention, the solution containing the compound of formula (Va) is concentrated to an oil.

Wherein the compound of formula (Iva) is reacted with greater than about 1 equivalent of sulfuryl chloride, the solution containing the compound of formula (Va) is preferably concentrated, according to known batch or continuous method, to remove at least about 70% of solvent mass.

Wherein the compound of formula (IVa) is reacted with about 1 equivalent of sulfuryl chloride, the solution containing the compound of formula (Va) is preferably concentrated, according to known batch or continuous method, to remove at least about 20% of solvent mass.

In an embodiment of the present invention, the solution containing the compound of formula (Va) is treated to remove volatiles. Suitable treatments include, but are not limited to vacuum distillation, concentration, stripping, passing through activated carbon or other absorbent, and the like.

The concentrate of the compound of formula (Va) is dissolved in a second organic solvent comprising at least the solvent used in step (Aa), preferably comprising at least one solvent selected from a cyclic ether, such as pyran, tetrahydrofuran, and the like; a straight or branched chain dialkyl ether such as glyme, MTBE, and the like; an aromatic hydrocarbon solvent such as toluene, benzene, xylene, and the like; or a mixture of a cyclic, straight or branched chain dialkyl ether and an aromatic hydrocarbon solvent. Preferably, the concentrate of the compound of formula (Va) is dissolved in the same organic solvent used in step (Aa) above.

Preferably, the concentrate of the compound of formula (Va) is dissolved to a final mass ratio of the solvent to the compound of formula (Va) in the range of from about 2:1 to about 10:1, more preferably to a mass ratio of the solvent to the compound of formula (Va) of about 6:1, to yield a reaction stream for use in step (Ba), hereinafter referred to as the third reaction stream, containing the compound of formula (Va).

In step (Ba), the compound of formula (Va) is reacted with ammonia, preferably ammonia gas;

in a second organic solvent comprising at least the solvent used in step (Aa);

wherein the second organic solvent comprises at least one solvent selected from a cyclic ether, such as pyran, tetrahydrofuran, and the like; a straight or branched chain dialkyl ether such as glyme, MTBE, and the like; an aromatic hydrocarbon solvent such as toluene, benzene, xylene, and the like; or a mixture of a cyclic, straight or branched chain dialkyl ether and an aromatic hydrocarbon solvent; preferably the second organic solvent comprises at least one solvent selected from a cyclic or straight or branched chain dialkyl ether such as THF, pyran, glyme, MTBE, and the like; more preferably the second organic solvent comprises at least glyme; more preferably still, the second organic solvent is the same as the first organic solvent; more preferably still, the second organic solvent is glyme;

wherein the ammonia is preferably present in an amount greater than about 1 molar equivalent of the compound of formula (Va); more preferably, the molar ratio of the ammonia to the compound of formula (Va) is greater than or equal to about 2:1; more preferably still, the molar ratio of the ammonia to the compound of formula (Va) is about 5:1;

wherein the temperature of the reaction is preferably maintained in the range of about −30° C. to about 50° C., more preferably in the range of about 0° C. to about 30° C., more preferably still at about 20° C.;

to form a solution of the compound of formula (III) and a precipitate.

Preferably, the ammonia gas is fed into the reactor at a controlled pressure or flow rate, more preferably at a pressure in the range of less than or equal to about 30 psia, more preferably still, at a pressure in the range of from about 15 to about 20 psia, more preferably still, at a pressure of about 19 psia.

In an embodiment of the present invention, the second organic solvent (used in step (Ba)) is selected from the group consisting of a cyclic ether, such as pyran, tetrahydrofuran, and the like; a straight or branched chain dialkyl ether such as glyme, MTBE, and the like; an aromatic hydrocarbon solvent such as toluene, benzene, xylene, and the like; or a mixture of a cyclic, straight or branched chain dialkyl ether and an aromatic hydrocarbon solvent. Preferably, the second organic solvent (used in step (Ba)) is selected from a cyclic or straight or branched chain dialkyl ether such as THF, pyran, glyme, MTBE, and the like, more preferably the second organic solvent (used in step (Ba)) is glyme.

In an embodiment of the present invention, the second organic solvent (used in Step (Ba)) is selected from the group consisting of a cyclic ether, a straight or branched chain dialkyl ether and an aromatic hydrocarbon solvent; wherein the second organic solvent is other than tetrahydrofuran or t-butyl methyl ether.

In another embodiment of the present invention, the second organic solvent (used in step (Ba)) comprises the solvent used in step (Aa) (i.e. the first organic solvent).

Preferably, the solution containing the compound of formula (III) and the precipitate is filtered by known methods, to remove the precipitate.

In an embodiment of the invention, the process for the preparation of a compound of formula (III) is run in two continuous stirred tank reactors (CSTRs). Preferably, step (Aa) is run such that the residence time in the first CSTR is about 1 hour. Preferably, step (Ba) is run such that the residence time in the second CSTR is about 3 hours. Preferably, step (Ba) is run such that the third reaction stream and ammonia are introduced above surface into the CSTR.

One skilled in the art will recognize that any of the processes of the present invention may be used to prepare racemic mixtures of a compound of the formula (I) or any of the stereoisomers of a compound of formula (I), by selection and substitution of appropriate racemic mixtures or stereoisomers of the reagents.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution.

The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following examples describe the invention in greater detail and are intended to illustrate the invention, but not to limit it.

EXAMPLE 1

Preparation of Diacetone-β-D-fructose Chlorosulfate (CS) Continuous Process

A DAF stock solution was prepared by weighing out diacetone-β-fructose (DAF) (911.0 g) into a one gallon glass bottle. To the solids were added glyme (2113.5 g, 2450 mL) and pyridine (290.7 g, 297 mL) and the solution was stirred to complete dissolution of the DAF. Additional stock solution was made as necessary.

A 1-liter Erlemeyer flask was filled with DAF stock solution (936.8 g, 987.2 mL) and placed on a top loading balance. A piston pump was configured to pump the solution into the reactor.

Into a separate flat-bottom boiling flask was weighed sulfuryl chloride (SC) (172.2 g, 103.8 mL) and the flask was immediately stoppered. The SC containing flask was then placed on a top loading balance and a second piston pump was set up to pump the SC into the reactor.

The reactor was a continuous stirred glass reactor with a four-necked head and a side overflow port at approximately the 1-liter level. A nitrogen pad utilizing a back-pressure bubbler was applied to the reactor. The material in the reactor from the previous experiment was determined to contain 0.3% DAF, 99.7% CS and 0.08% other unidentified material.

The piston pump for the SC was started at a feed rate of 2.2 g per min. When the SC reached the reactor, the piston pump for the DAF stock solution was started at a feed rate of 15.2 g per min.

The reactor cooling system was set at −15° C. in an attempt to maintain the reaction temperature near 0° C. during the course of the reaction; a temperature in the range of +4.0° C. to +5.0° C. was achieved. The reactor was stirred at 400 rpm.

The reactor was run continuously for a period of seven (7) hours, with the SC and DAF stock solution feed reservoirs replenished as required. Balance readings were used to monitor addition rates and the pump settings adjusted to maintain feed rates. The residence time within the reactor was calculated at about one (1) hour.

The receiving flask was replaced hourly, with the product stream filtered and then evaporated to an oil on a rotary evaporator with a water bath maintained at a temperature of about 40° C. Each aliquot of concentrated oil was transferred to a glass bottle and placed in a freezer at −20° C. for storage.

The product stream from the reactor was also sampled hourly and analyzed via GC with results as listed in Table 1, below:

TABLE 1

| Product Stream Contents | | |
|---|---|---|
| Time | % CS | % DAF |
| 1 hr | 99.2 | 0.8 |
| 2 hr | 99.5 | 0.5 |
| 3 hr | 99.6 | 0.4 |
| 4 hr | 99.7 | 0.3 |
| 5 hr | 99.8 | 0.2 |
| 6 hr | 99.8 | 0.2 |
| 7 hr | 99.8 | 0.2 |

EXAMPLE 2

Preparation of Topiramate (TPM) Continuous Process

CS feed solution was prepared by reconstituting the oil prepared as in Example 1, by dissolving in glyme to a final concentration of 1 gm CS to 5.8 gms glyme as follows. The CS oil (376.1 g) was removed from the freezer (where it was stored between runs to avoid decomposition) and allowed to warm to room temperature. The CS was rinsed into a 4-liter Erlemeyer flask with portions of glyme. Glyme was added to the desired ratio, for a total glyme addition of 2181.33 gms. The solution was mixed well and filtered through a 934-AH glass-fiber filter pad using mild vacuum, to yield a CS stock solution (2523.2 g).

A 2-liter stainless steel reactor with overflow port at about the 1.5 liter level was isolated from a 20 liter stainless steel product receiver. The product receiver was evacuated to a vacuum of 30" Hg using a water aspirator.

The reactor cooling system was set to 16.5° C. and was thereafter adjusted in stages to a final setting of 13° C. to maintain the interior reaction temperature between 17.9° C. and 19.9° C. during the course of the reaction. The reactor was stirred at 700 rpm.

The entire reactor system was pressurized to about 2 psig (17 psia) with anhydrous ammonia. During the reaction run, the ammonia was continuously added under pressure control, maintaining a system pressure level of between 2 psig (17 psia) and 3 psig (18 psia). The measured ammonia pressure was in the range of 1.5 psig (16.2 psia) to 2.5 psig (17.2 psia).

The CS feed solution was weighed before and after use. The reservoir containing the CS feed solution was placed on a top loading balance and a stream of nitrogen was maintained at the surface of the liquid. The CS feed solution was continuously added to the reactor via a piston pump at a rate of about 7.1 g per min. As more CS feed solution was needed, it was prepared as previously described and the reservoir replenished.

The reactor was run continuously for sixteen (16) hours, with overflow collected in the product receiver can. The overflow was monitored by HPLC for composition, including amount of product (Topiramate), amount of DAF, amount of CS, and amount of "other" byproducts, with results as listed in Table 2, below.

TABLE 2

Product Stream Contents

| Time | % Topiramate | % CS | % DAF | % Other |
|---|---|---|---|---|
| 1 hr | 94.1 | 4.6 | 1.2 | 0.1 |
| 2 hr | 94.2 | 4.3 | 1.4 | 0.1 |
| 3 hr | 91.5 | 6.2 | 2.1 | 0.2 |
| 4 hr | 89.5 | 6.9 | 3.3 | 0.3 |
| 5 hr | 89.8 | 7.1 | 3.0 | 0.1 |
| 6 hr | 90.4 | 7.2 | 2.4 | 0.0 |
| 7 hr | 90.9 | 6.8 | 2.2 | 0.1 |
| 8 hr | 91.5 | 6.3 | 2.0 | 0.2 |
| 9 hr | 91.7 | 6.3 | 1.8 | 0.2 |
| 10 hr | 92.1 | 6.0 | 1.7 | 0.2 |
| 11 hr | 92.1 | 6.1 | 1.6 | 0.2 |
| 12 hr | 91.7 | 6.6 | 1.4 | 0.3 |
| 13 hr | 90.8 | 7.8 | 1.3 | 0.1 |
| 14 hr | 91.1 | 7.5 | 1.2 | 0.2 |
| 15 hr | 91.6 | 6.8 | 1.1 | 0.5 |
| 16 hr | 90.6 | 8.0 | 1.1 | 0.3 |

After 16 hours, the reactor was turned off and the product receiver can was allowed to sit under ammonia pressure of about 2.0 psig (17 psia) for about 8 hours. The product receiver can was then vented to allow most of the ammonia to escape.

The product slurry was filtered in a Buchner funnel. The solids were slurried in the Buchner funnel and drained thoroughly with two nearly equal portions of fresh glyme (total weight 172.2 g). The filtered contents of the product receiver can and washings weighed 6321.8 g, while the wetcake of washed solids weighed 194.6 gms.

The filtered solution was evaporated to an oil on a rotary evaporator with a water bath maintained at a temperature of 40° C. to yield crude Topiramate.

GC analysis of the solution in the product receiver after sixteen (16) hours reaction time showed a mixture of 1.1 Area % DAF, 8.0 Area % CS, 90.6 Area % TPM and 0.3 Area % unknowns.

GC analysis of the solution in the product receiver after sixteen (16) hours reaction time and about 8 hours standing showed a mixture of 0.9 Area % DAF, no CS, 98.5 Area % TPM and 0.6 Area % unknowns.

GC analysis of the contents of the product receiver after filtration showed a mixture of 1.7 Area % DAF, no CS, 97.9 Area % TPM and 0.5 Area % unknowns.

EXAMPLE 3

Preparation of Diacetone-β-D-fructose Chlorosulfate (CS) Continuous Process

The reactor used was a continuously stirred glass reactor with a four-necked head, a side overflow port at approximately the 1-liter level, and a nitrogen pad utilizing a back-pressure bubbler. The reactor was cooled with an indirect glycol cooling system. Prior to the start of the experiment, the material in the reactor was analyzed by GC. The starting reactor compositions for completed runs were as summarized in Table 3.

TABLE 3

Starting Reactor Composition

| | Run# | | | | | | |
|---|---|---|---|---|---|---|---|
| | 1 | 2 | 3 | 4 | 5 | 6 | 7 |
| % CS | 99.0 | 99.6 | 94.6 | 97.9 | 99.6 | 99.4 | 99.6 |
| % DAF | 1.0 | 0.4 | 5.4 | 2.1 | 0.3 | 0.6 | 0.4 |
| % "Other" | 0 | 0 | 0 | 0 | 0.1 | 0 | 0 |

A 1-liter Erlenmeyer flask was filled with DAF stock solution (prepared as described in Example 1) and was placed on a top loading balance. A piston pump was configured to pump the solution into the reactor. Sulfuryl chloride (SC) was weighed into a separate flat-bottom boiling flask. The flask containing the sulfuryl chloride was stoppered and then placed on a top loading balance. A second piston pump was configured to pump the SC into the reactor.

Agitation was started at about 400 rpm, and the piston pump for the SC was started at the desired feed rate. When the SC reached the reactor, the piston pump for the DAF stock solution was started at the desired rate. The reactor was run continuously for a set period of hours, with the SC and DAF stock solutions feed reservoirs replenished as required. The reactor product overflowed continuously to a product receiver that was emptied as needed. Balance readings were used to monitor addition rates and the pump settings adjusted to maintain feed rates. Operating conditions, including the calculated reactor residence times, were as summarized in Table 4, below.

TABLE 4

Reactor Operating Conditions

| | Run # | | | | | | |
|---|---|---|---|---|---|---|---|
| | 1 | 2 | 3 | 4 | 5 | 6 | 7 |
| Mole Ratio SO$_2$Cl$_2$:DAF | 1.05 | 0.94 | 0.93 | 1.01 | 1.00 | 1.00 | 0.99 |
| Mole Ratio Pyridine:DAF | 1.05 | 1.05 | 1.05 | 1.05 | 1.05 | 1.05 | 1.05 |
| Mole Ratio Glyme:DAF | 2.32 | 2.32 | 2.32 | 2.32 | 4.64 | 4.64 | 4.64 |
| Pump rate (g/min) Glyme:DAF | 7.61 | 7.62 | 15.4 | 15.2 | 13.4 | 13.4 | 13.4 |
| Pump rate (g/min) SO$_2$Cl$_2$:DAF | 1.14 | 1.02 | 2.02 | 2.17 | 1.17 | 1.17 | 1.15 |

TABLE 4-continued

Reactor Operating Conditions

| | Run # | | | | | | |
|---|---|---|---|---|---|---|---|
| | 1 | 2 | 3 | 4 | 5 | 6 | 7 |
| Reaction Temp (° C.) | −1 | −2 | 2 | 4 | 0 | 14 | 30 |
| Residence Time (hrs) | 2.0 | 2.0 | 1.0 | 1.0 | 1.0 | 1.0 | 1.0 |

The reactor was sampled hourly and the samples analyzed for content by GC. The hours of operation at each condition and the resulting reactor content near completion of the continuous operation are summarized in Table 5, below.

TABLE 5

Operating Time & Reactor Contents

| | Run # | | | | | | |
|---|---|---|---|---|---|---|---|
| | 1 | 2 | 3 | 4 | 5 | 6 | 7 |
| Hrs of operation | 5 | 5 | 5 | 5 | 4 | 5 | 3 |
| % CS | 99.3 | 94.1 | 91.5 | 99.5 | 99.5 | 98.8 | 95.9 |
| % DAF | 0.7 | 5.9 | 8.5 | 0.5 | 0.5 | 1.2 | 4.1 |
| % "Other" | 0 | 0 | 0 | 0 | 0 | 0 | 0 |

EXAMPLE 4

Preparation of Topiramate (TPM) Continuous Process

The continuous reactor was a 2-liter stainless steel pressure reactor with an overflow port at about the 1.5 liter level. The product receiver was a 20-liter stainless steel pressure tank. The reactor was cooled with an indirect glycol cooling system to maintain the temperature near the targeted temperature during the course of the reaction. Prior to the start of the experiment, the material in the reactor from the previous experiment was analyzed by GC to determine content. The starting reactor compositions were summarized in Table 6, below.

TABLE 6

Reactor Contents at Start of Experiment

| | Run # | | | | | | | | | | | | |
|---|---|---|---|---|---|---|---|---|---|---|---|---|---|
| | 10 | 11 | 12 | 13 | 14 | 15 | 16 | 17 | 18 | 19 | 20 | 21 | 22 |
| % TOP | 77.5 | 88.2 | 91.9 | 83.0 | 96.6 | 92.2 | 95.0 | 89.1 | 85.4 | 85.7 | 96.0 | 89.8 | 81.7 |
| % CS | 0 | 0 | 0 | 0 | 0 | 0 | 0 | 0 | 0 | 0 | 0 | 0 | 0 |
| % DAF | 23.3 | 11.7 | 6.3 | 15.1 | 3.2 | 7.0 | 4.8 | 10.3 | 14.5 | 14.3 | 2.6 | 9.6 | 17.8 |

At the start of the experiment, the product receiver was evacuated and the entire reactor system was pressurized to the target pressure with anhydrous ammonia gas. With the exception of Run #10, the ammonia was added above surface. A reservoir containing CS solution, prepared as described in Example 2, was placed on a top loading balance and blanketed (inerted) with nitrogen. A piston pump was configured to pump the CS solution continuously into the reactor. With the exception of Run #10 and #11, the CS solution was added to the reactor above surface.

The piston pump for the CS solution was started at the target feed rate. Ammonia was continuously added under pressure control to maintain the target pressure. The reactor product overflowed continuously to the product receiver. As more CS feed solution was needed, it was prepared as described in Example 2. Operating conditions, including the calculated reactor residence time, were summarized in Table 7, below.

TABLE 7

Reactor Operating Conditions

| | Run # | | | | | | | | | | | | |
|---|---|---|---|---|---|---|---|---|---|---|---|---|---|
| | 10 | 11 | 12 | 13 | 14 | 15 | 16 | 17 | 18 | 19 | 20 | 21 | 22 |
| Mass Ratio Glyme:CS oil | 2.9 | 5.8 | 4.3 | 8.7 | 5.8 | 5.8 | 5.8 | 5.8 | 2.9 | 2.9 | 5.8 | 5.8 | 5.8 |

TABLE 7-continued

Reactor Operating Conditions

| | Run # | | | | | | | | | | | | |
|---|---|---|---|---|---|---|---|---|---|---|---|---|---|
| | 10 | 11 | 12 | 13 | 14 | 15 | 16 | 17 | 18 | 19 | 20 | 21 | 22 |
| % DAF in CS solution | 7.0 | 2.3 | 3.3 | 3.0 | 1.8 | 1.3 | 1.1 | 2.1 | 1.5 | 2.0 | 1.0 | 1.0 | 5.6 |
| CS solution Feed Rate (g/min) | 7.4 | 7.0 | 7.4 | 7.3 | 7.1 | 7.2 | 7.7 | 7.2 | 7.7 | 7.7 | 4.2 | 4.2 | 4.3 |
| $NH_3$ pressure at reactor (psia) | 30 | 28 | 17 | 17 | 4 | 5 | 17 | 30 | 18 | 4 | 17 | 18 | 30 |
| Agitator speed (rpm) | 350 | 300 | 720 | 715 | 680 | 686 | 688 | 703 | 697 | 732 | 690 | 720 | 722 |
| Reactor Temp (° C.) | 0 | 20 | 19 | 18 | 19 | 0 | 19 | 19 | 19 | 20 | 18 | 0 | 19 |
| Residence time (hr) | 3.0 | 3.1 | 3.1 | 3.0 | 3.0 | 3.0 | 2.8 | 3.0 | 2.9 | 2.9 | 5.1 | 5.2 | 5.0 |

The reactor contents were sampled hourly and the samples analyzed for content by GC. The hours of operation at each condition and the resulting reactor content near completion of the continuous operation were as summarized in Table 8, below.

TABLE 8

Operating Time and Reactor Contents

| | Run | | | | | | | | | | | | |
|---|---|---|---|---|---|---|---|---|---|---|---|---|---|
| | 10 | 11 | 12 | 13 | 14 | 15 | 16 | 17 | 18 | 19 | 20 | 21 | 22 |
| Operating time (hrs) | 6 | 7 | 6 | 9 | 9 | 5 | 8 | 9 | 6 | 8 | 15 | 10 | 15 |
| % Topiramate | 72.9 | 83.0 | 77.9 | 82.2 | 77.0 | 84.9 | 90.6 | 84.0 | 75.6 | 73.2 | 87.5 | 89.8 | 84.6 |
| % CS | 0.1 | 1.9 | 4.0 | 6.0 | 17.3 | 10.0 | 5.3 | 1.7 | 7.4 | 16.7 | 3.0 | 6.3 | 1.5 |
| % DAF | 25.3 | 15.0 | 16.2 | 9.9 | 5.1 | 4.6 | 4.0 | 14.2 | 15.4 | 9.6 | 8.9 | 3.1 | 13.1 |

EXAMPLE 5

Effect of Solvent Removal

STEP A: Preparation of Diacetone Fructose Chlorosulfate Using a Stoichiometric Amount of $SO_2Cl_2$ A 5000 mL 3-neck round spherical flask was fitted with mechanical stirrer, thermometer and an addition funnel connected to a low pressure nitrogen source to provide an inert atmosphere. DAF (825 g, 3.17 moles), glyme (1915 g) and pyridine (263.5 g, 3.33 moles) were added to the flask and stirred at 25° C. to complete dissolution. The flask was cooled in a salt and ice mixture to an internal temperature of about 0° C. Sulfuryl chloride (427.9 g, 3.17 moles) was added over 4 hours while maintaining the reaction temperature at 0° C. The mixture was stirred at 0° C. for an additional 15 minutes, after which time the bath was removed and the mixture warmed to room temperature. The contents were sampled and analyzed by GC.

Analysis: 1.19% DAF, 98.78% CS

The mixture was vacuum filtered to remove the pyridine hydrochloride solids. The CS solution (2835 g) was transferred to a bottle, tightly capped and stored at −20° C. until used in Step B.

Step B: Preparation of CS Solution for Conversion to Topiramate

The solution prepared as in Step A above (130 g) was evaporated in vacuo, in a 250 mL round bottom flask on a rotary evaporator and 40° C. water bath, until 20% of the solvent was removed.

Following concentration, the flask contents were diluted to the original 130 g with fresh glyme, mixed, vacuum filtered, and kept under nitrogen until used in Step C.

Step C: Conversion of CS Solution to Topiramate

A clean, dry 300 mL stirred Parr reactor (316SS) was purged with nitrogen, then evacuated and isolated. Fresh glyme (87 g) was transferred into the vessel which was briefly re-evacuated. The stirrer was turned on and the system was pressurized with ammonia to about 2 psig. A water bath was used with additions of ice as needed to maintain the contents at about 15–20° C. throughout the reaction period. The CS feed from Step B was added via pump over about 1.25 hours, then stirred an additional 2 hours at about 15–20° C. under 2 psig ammonia pressure.

The reactor contents were vacuum filtered to remove $NH_4Cl$ and the clear filtrate analyzed by GC.

Analysis: 9.5% DAF, 90.0% TPM

EXAMPLE 6

Effect of Solvent Removal

STEP A: Preparation of Diacetone Fructose Chlorosulfate Using 5% Excess Amount of $SO_2Cl_2$ A 5000 mL 3-neck round spherical flask was fitted with mechanical stirrer, thermometer and an addition funnel connected to a low pressure nitrogen source to provide an inert atmosphere. DAF (825 g, 3.17 moles), glyme (1915 g) and pyridine (263.5 g, 3.33 moles) were added to the flask and stirred at 25° C. to complete dissolution. The flask was cooled in a salt and ice mixture to an internal temperature of about 0° C. Sulfuryl chloride (449.5 g, 3.33 moles) was added over 4 hours while maintaining the reaction temperature at 0° C. The mixture was stirred at 0° C. for an additional 15 minutes, after which time the bath was removed and the mixture warmed to room temperature. The contents were sampled and analyzed by GC.

Analysis: 0.23% DAF, 99.72% CS

The mixture was vacuum filtered to remove the pyridine hydrochloride solids. The CS solution (2859 g) was transferred to a bottle, tightly capped and stored at −20° C. until used in Step B.

Step B: Preparation of CS Solution for Conversion to Topiramate

A portion of the solution prepared in Step B above (130 g) was evaporated in vacuo, in a 250 mL round bottom flask on a rotary evaporator and 40° C. water bath, until 70% of the solvent was removed.

Following concentration, the flask contents were diluted to the original 130 g with fresh glyme, mixed, vacuum filtered, and kept under nitrogen until used in Step C.

Step C: Conversion of CS Solution to Topiramate

A clean, dry 300 mL stirred Parr reactor (316SS) was purged with nitrogen, then evacuated and isolated. Fresh glyme (87 g) was transferred into the vessel which was briefly re-evacuated. The stirrer was turned on and the system was pressurized with ammonia to about 2 psig. A water bath was used with additions of ice as needed to maintain the contents at about 15–20° C. throughout the reaction period. The CS feed from Step B was added via pump over about 1.25 hours, then stirred an additional 2 hours at about 15–20° C. under 2 psig ammonia pressure.

The reactor contents were vacuum filtered to remove $NH_4Cl$ and the clear filtrate analyzed by GC.

Analysis: 8.1% DAF, 90.0% TPM

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A continuous process for the preparation of a compound of formula (I)

wherein
X is selected from $CH_2$ or O;
$R^1$ is selected from the group consisting of hydrogen and $C_{1-4}$alkyl;
$R^3$, $R^4$, $R^5$ and $R^6$ are each independently selected from hydrogen or lower alkyl and, when X is $CH_2$, $R^5$ and $R^6$ may be alkene groups joined to form a benzene ring and, when X is O, $R^3$ and $R^4$ and/or $R^5$ and $R^6$ together may be a methylenedioxy group of the formula:

wherein
$R^7$ and $R^8$ are same or different and are hydrogen, lower alkyl or are alkyl and are joined to form a cyclopentyl or cyclohexyl ring;
comprising (A) reacting a suitably substituted compound of formula (IV) with sulfuryl chloride;
in the presence of an organic or inorganic base;
in a first organic solvent;
to form the corresponding compound of formula (V); and (B) continuously reacting the compound of formula (V) with a suitably substituted compound of formula (VI);
in a second organic solvent;
wherein the first organic solvent and the second organic solvent are each glyme;
to form the corresponding compound of formula (I).

2. The process as in claim 1, wherein the organic or inorganic base is an organic base.

3. The process as in claim 2, wherein the organic base is pyridine.

4. The process as in claim 1, wherein the sulfuryl chloride is present in an amount greater than about 0.9 moles per mole of the compound of formula (IV).

5. The process as in claim 1, wherein the base is present in an amount greater than about 1 molar equivalent of the compound of formula (IV).

6. The process as in claim 5, wherein the molar ratio of the compound of formula (IV) to the base is at least about 1:1.05.

7. The process as in claim 1, wherein the temperature of the reaction in Step (A) is less than about 50° C.

8. The process as in claim 1, wherein the compound of formula (VI) is present in an amount greater than about 1 molar equivalent of the compound of formula (V).

9. The process as in claim 8, wherein the molar ratio of the compound of formula (VI) to the compound of formula (V) is at least about 2:1.

10. The process as in claim 1, wherein the compound of formula (VI) is ammonia and the ammonia is fed into the reactor at a pressure of about 19 psia.

11. The process as in claim 1, wherein the temperature of the reaction in Step (B) is in the range of from about −30 to about 50° C.

12. The process as in claim 1, wherein the compound of formula (V) is formed in a solution comprising the compound of formula (V) and the first organic solvent.

13. The process as in claim 12, wherein the sulfuryl chloride is reacted in amount equal to about 1 equivalent relative to the compound of formula (IV), further comprising concentrating the solution comprising the compound of formula (V) and the first organic solvent to remove at least about 20% of the solvent mass.

14. The process as in claim 12, wherein the sulfuryl chloride is reacted in amount greater than about 1 equivalent relative to the compound of formula (IV), further comprising concentrating the solution comprising the compound of formula (V) and the first organic solvent to remove at least 70% of the solvent mass.

15. The process as in claim 12, further comprising concentrating the solution comprising the compound of formula (V) and the first organic solvent to an oil.

16. The process as in claim 12, further comprising treating the solution comprising the compound of formula (V) and the first organic solvent to remove volatiles.

17. The process as in claim 1, wherein step (A) and step (B) are each run in a continuous stirred tank reactor.

18. A continuous process for the preparation of a compound of formula (III)

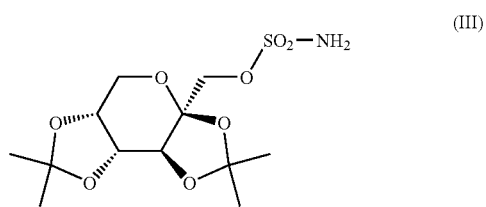

comprising

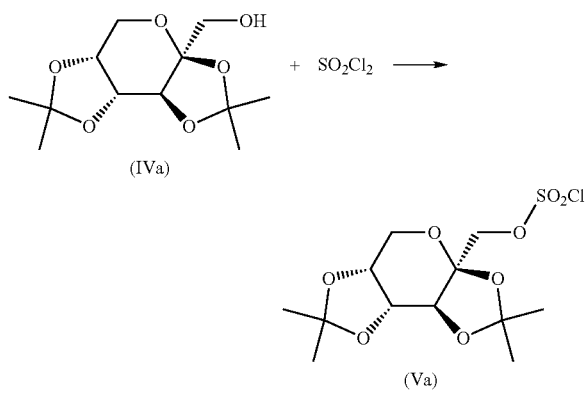

(Aa) reacting a compound of formula (IVa) with sulfuryl chloride;
in the presence of an organic or inorganic base;
in a first organic solvent;
to form the corresponding compound of formula (Va); and

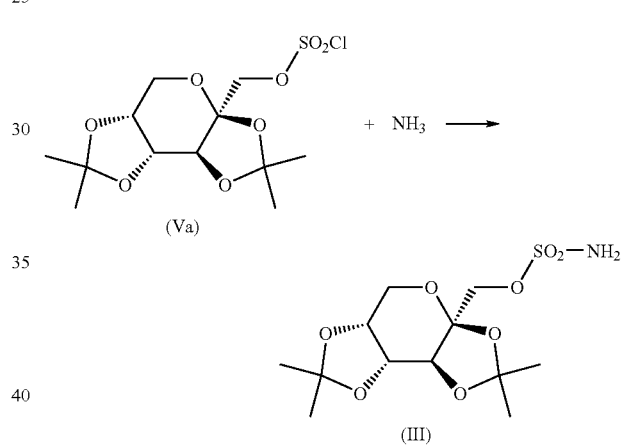

(Ba) reacting the compound of formula (Va) with ammonia;
in a second organic solvent;
wherein the first organic solvent and the second organic solvent are each glyme;
to form the corresponding compound of formula (III).

19. The process as in claim 18, wherein the organic or inorganic base is an organic base.

20. The process as in claim 19, wherein the organic base is pyridine.

21. The process as in claim 18 wherein the sulfuryl chloride is present in an amount greater than about 0.9 moles per mole of the compound of formula (IVa).

22. The process as in claim 18, wherein the base is present in an amount greater than about 1 molar equivalent of the compound of formula (IVa).

23. The process as in claim 22, wherein the molar ratio of the compound of formula (Iva) to the base is at least about 1:1.05.

24. The process as in claim 18, wherein the temperature of the reaction in Step (Aa) is less than about 50° C.

25. The process as in claim 18, wherein the ammonia is present in an amount greater than about 1 molar equivalent of the compound of formula (Va).

26. The process as in claim 25, wherein the molar ratio of the ammonia to the compound of formula (Va) is at least about 2:1.

27. The process as in claim 18, wherein ammonia is fed into the reactor at a pressure of about 19 psia.

28. The process as in claim 18, wherein the temperature of the reaction in Step (Ba) is in the range of from about −30 to about 50° C.

29. The process as in claim 18, wherein the compound of formula (Va) is formed in a solution comprising the compound of formula (Va) and the first organic solvent.

30. The process as in claim 29, wherein the sulfuryl chloride is reacted in amount equal to about 1 equivalent relative to the compound of formula (IVa), further comprising concentrating the solution comprising the compound of formula (Va) and the first organic solvent to remove at least about 20% of the solvent mass.

31. The process as in claim 29, wherein the sulfuryl chloride is reacted in amount greater than about 1 equivalent relative to the compound of formula (IVa), further comprising concentrating the solution comprising the compound of formula (Va) and the first organic solvent to remove at least 70% of the solvent mass.

32. The process as in claim 29, further comprising concentrating the solution comprising the compound of formula (Va) and the first organic solvent to an oil.

33. The process as in claim 29, further comprising treating the solution comprising the compound of formula (Va) and the first organic solvent to remove volatiles.

34. The process as in claim 18, wherein step (Bb) is run in a continuous stirred tank reactor.

35. The process as in claim 18, wherein step (Aa) and step (Ba) are each run in a continuous stirred tank reactor.

* * * * *